(12) United States Patent
Avinash et al.

(10) Patent No.: US 7,920,729 B2
(45) Date of Patent: Apr. 5, 2011

(54) CLASSIFICATION METHODS AND APPARATUS

(75) Inventors: Gopal B. Avinash, Menomonee Falls, WI (US); Kenny Kishan Israni, Chicago, IL (US); Baojun Li, Waukesha, WI (US)

(73) Assignee: General Electric Co., Schenectady, NY (US)

( * ) Notice: Subject to any disclaimer, the term of this patent is extended or adjusted under 35 U.S.C. 154(b) by 1183 days.

(21) Appl. No.: 11/463,845

(22) Filed: Aug. 10, 2006

(65) Prior Publication Data
US 2008/0037846 A1 Feb. 14, 2008

(51) Int. Cl.
*G06K 9/00* (2006.01)
*A61B 6/00* (2006.01)

(52) U.S. Cl. .......................................... 382/128; 378/21
(58) Field of Classification Search .......... 382/128–134, 382/145, 159, 165, 170, 224, 225, 227; 378/4, 378/21–27, 46, 90, 92, 98.4, 98.6, 98.9, 101, 378/140, 901; 600/407, 408, 425; 128/925, 128/920
See application file for complete search history.

(56) References Cited

U.S. PATENT DOCUMENTS

| 5,375,175 | A | | 12/1994 | Kino et al. |
| 5,872,828 | A | * | 2/1999 | Niklason et al. ................ 378/23 |
| 6,058,322 | A | * | 5/2000 | Nishikawa et al. ........... 600/408 |
| 7,058,210 | B2 | * | 6/2006 | Mundy et al. ................. 382/128 |
| 2005/0185824 | A1 | | 8/2005 | Chen |
| 2006/0210131 | A1 | * | 9/2006 | Wheeler et al. ............... 382/128 |

* cited by examiner

*Primary Examiner* — Abolfazl Tabatabai

(57) ABSTRACT

A method includes using a point spread function based rule to classify regions in a dataset.

13 Claims, 7 Drawing Sheets

CLASSIFICATION METHODS AND APPARATUS

BACKGROUND OF THE INVENTION

This invention relates generally to x-ray methods and apparatus, and more particularly to methods and apparatus that provide for the classification of structures in a dataset.

Digital Tomosynthesis is widely used for three-dimensional (3D) reconstruction of objects acquired from limited angle x-ray projection imaging with a stationary digital detector. It is a refinement of conventional geometric tomography, which has been known since the 1930s. As with geometric tomography, tomosynthesis suffers from the residual blur of objects outside the plane of interest. This tomographic blur from overlying anatomy obscures detail in the plane of interest and limits the contrast enhancement of the slices. Removing the overlying blurred anatomic structures improves contrast of in-plane structures by restricting the dynamic range of the image to that of the section of interest, as well as by removing residual structures that may have frequency content similar to that of some objects of interest in that section. At a fundamental level, the point-spread function (PSF) of a tomosynthesis dataset characterizes the spread of blur in the imaging volume, and is shift-variant in nature. However, removing the complete blur is a non-trivial task. It is computationally intensive and because of the extent of the PSF, it is not easy to eliminate blur.

BRIEF DESCRIPTION OF THE INVENTION

In one aspect, a method includes using a point spread function based rule to classify regions in a dataset.

In yet another aspect, a computer readable medium is provided that is embedded with a program that is configured to instruct a computer to use a point spread function based rule to classify regions in a dataset.

In another aspect, a system includes an x-ray source, an x-ray detector positioned to receive x-rays emitted from the source, and a computer operationally coupled to the source and the detector. The computer is configured to use a point spread function to classify structures in a dataset.

In still another aspect, a method includes providing an object to be scanned, scanning the object to obtain a dataset, and using a point spread function based rule to classify regions in the dataset.

In yet another aspect, a method includes accessing a dataset, and using a point spread function based rule to classify regions in the dataset.

DETAILED DESCRIPTION OF THE INVENTION

There are herein described methods and apparatus useful for imaging systems such as, for example, but not limited to an x-ray tomosynthesis system. The apparatus and methods are illustrated with reference to the figures wherein similar numbers indicate the same elements in all figures. Such figures are intended to be illustrative rather than limiting and are included herewith to facilitate explanation of an exemplary embodiment of the apparatus and methods of the invention. Although, described in the setting of an x-ray tomosynthesis system, it is contemplated that the benefits of the invention accrue to all systems with x-ray sources. One purpose of this disclosure is to provide a classification framework that decomposes a tomosynthesis dataset into multiple categories based on the nature of the PSF. This classification can guide the selection of processing paths described in patent application Ser. No. 11/464,103 co-filed even date with this disclosure.

Figure 1:
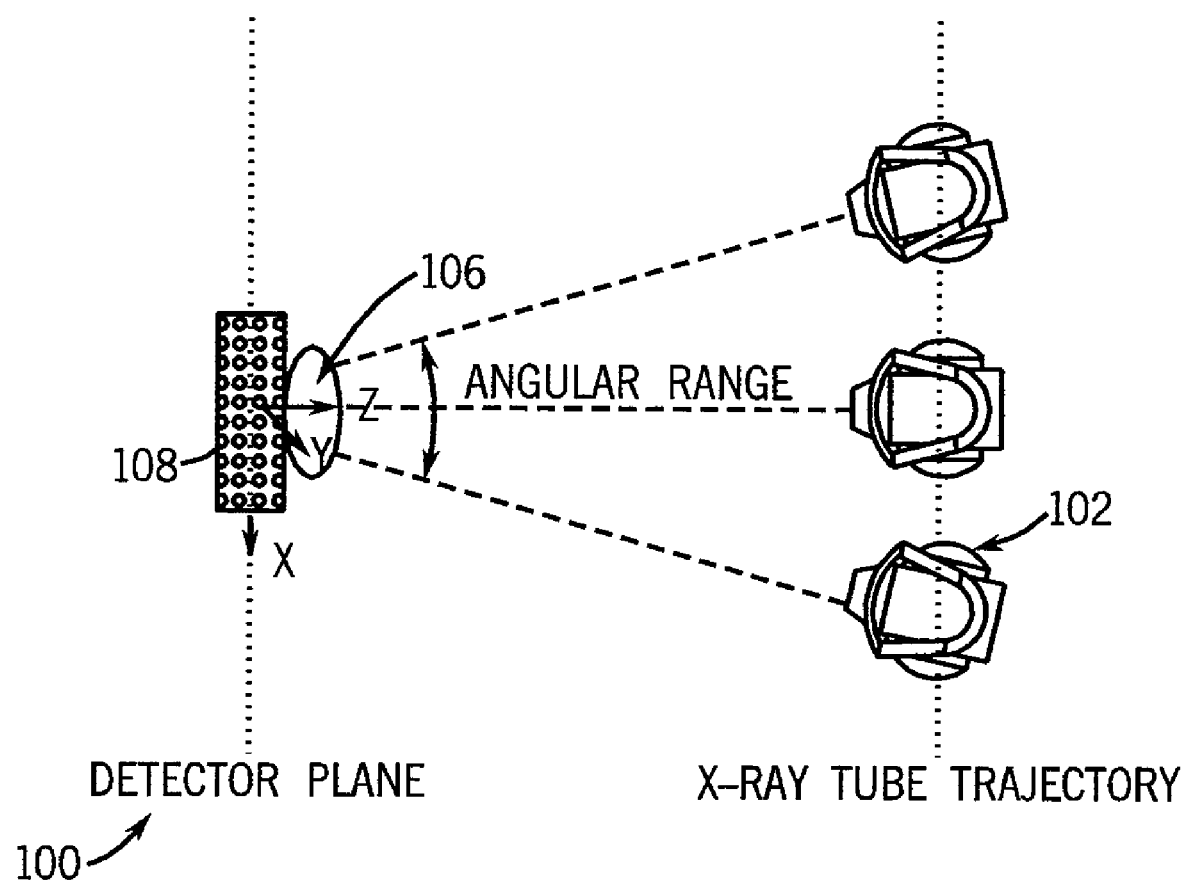
FIG. 1 illustrates an exemplary x-ray imaging system.

FIG. 1 illustrates an exemplary x-ray tomosynthesis imaging system 100. The imaging system 100 includes an x-ray source 102, which subjects the structure under examination 106 to x-ray photons. As examples, the x-ray source 102 may be an x-ray tube, and the structure under examination 106 may be a human patient, test phantom, and/or other inanimate object under test.

The x-ray imaging system 100 also includes a detector 108 coupled to a processing circuit. The processing circuit (e.g., a microcontroller, microprocessor, custom ASIC, or the like) is coupled to a memory and a display device. The memory (e.g., including one or more of a floppy disk drive, CD-ROM drive, DVD drive, magnetic optical disk (MOD) device, or any other digital device including a network connecting device such as an Ethernet device for reading instructions and/or data from a computer-readable medium, such as a floppy disk, or an other digital source such as a network or the Internet, as well as yet to be developed digital means, and the like) stores imaging data.

The memory may also store a computer program including instructions executed by the processing circuit to implement the functions described herein. The processing circuit provides an image for display on a device. As described in further detail herein, the image may representative of different structures (e.g., soft-tissue, bone). The detector 108 may be a flat panel solid state image detector, for example, although conventional film images stored in digital form in the memory may also be processed. In one embodiment, the processing circuit executes instructions stored in firmware (not shown). Generally, a processor is programmed to execute the processes described below.

Of course, the methods described herein are not limited to practice in system 100 and can be utilized in connection with many other types and variations of imaging systems. In one embodiment, the processing circuit is a computer that is programmed to perform functions described herein, accordingly, as used herein, the term computer is not limited to just those integrated circuits referred to in the art as computers, but broadly refers to computers, processors, microcontrollers, microcomputers, programmable logic controllers, application specific integrated circuits, and other programmable circuits. Although the herein described methods are described in a human patient setting, it is contemplated that the benefits of the invention accrue to non-human imaging systems such as those systems typically employed in small animal research.

As used herein, an element or step recited in the singular and proceeded with the word "a" or "an" should be understood as not excluding plural said elements or steps, unless such exclusion is explicitly recited. Furthermore, references to "one embodiment" of the present invention are not intended to be interpreted as excluding the existence of additional embodiments that also incorporate the recited features.

Also, as used herein, the phrase "reconstructing an image" is not intended to exclude embodiments of the present invention in which data representing an image is generated but a viewable image is not. Therefore, as used herein the term, "image," broadly refers to both viewable images and data representing a viewable image. However, many embodiments generate (or are configured to generate) at least one viewable image.

Although the herein described methods are described in a medical setting, it is contemplated that the benefits of the invention accrue to non-medical imaging systems such as those systems typically employed in an industrial setting or a transportation setting, such as, for example, but not limited to, a baggage scanning system for an airport or other transportation center.

A novel methodology was developed to classify the tomosynthesis imaging volume into in-focus, out-of-focus, background, and low-frequency structures based on the intensity profiles generated across the reconstructed slices.

Figure 2A:
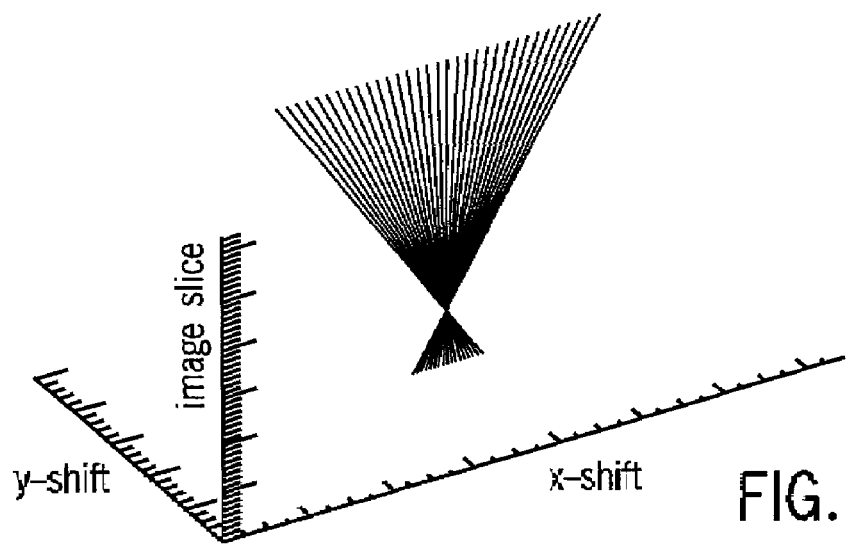
FIG. 2 illustrates the three-dimensional PSF at different locations in the reconstructed volume.
Figure 2B:
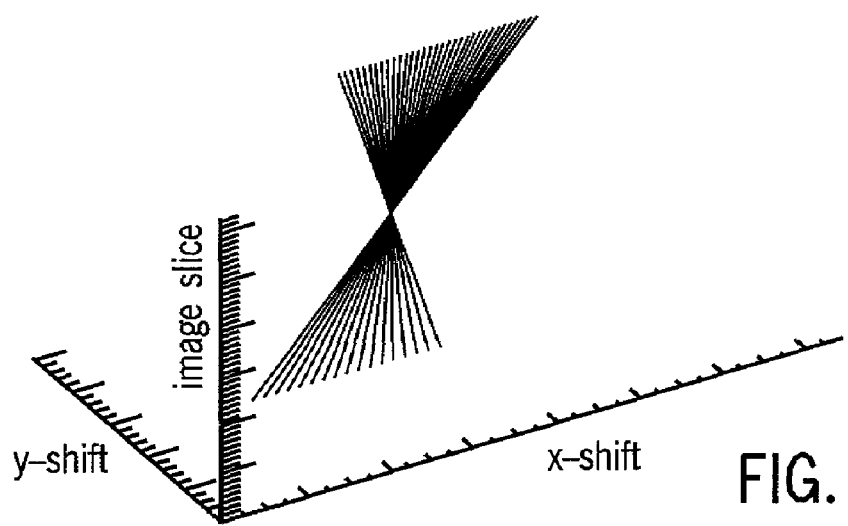
Figure 2C:
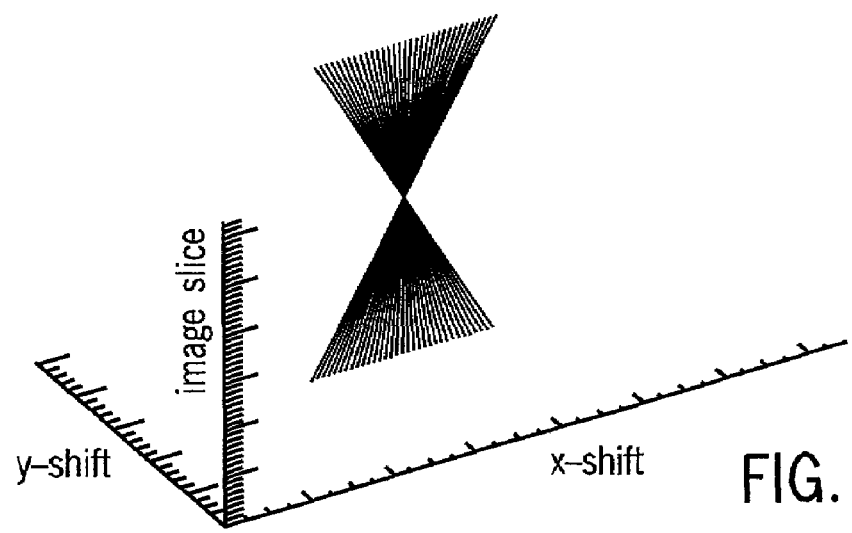

A linear digital tomosynthesis geometry and a backprojection algorithm were considered for the reconstruction. However, it is contemplated that the benefits of the invention accrue to all cases where the PSF is shift variant, and equally applicable to a circular geometry and reconstruction techniques other than backprojection. The three-dimensional PSF at every point in the imaging volume was determined and characterized with respect to its shape and intensity (See Avinash et. al, Mar. 2, 2006, "CHARACTERIZATION OF POINT SPREAD FUNCTION IN LINEAR DIGITAL TOMOSYNTHESIS: A SIMULATION STUDY", SPIE Volume 6142). The intensity profile of the PSF plays an important role in the classification technique. These intensity weights are linearly interpolated at every slice in the PSF considering finite detector resolution. If correctly done, the integral of weights for every slice in the PSF equals the number of projection rays (N) passing through the current pixel (for which the PSF is estimated). The shift-variant PSF at different locations in the imaging volume is shown in FIG. 2.

Figure 3A:
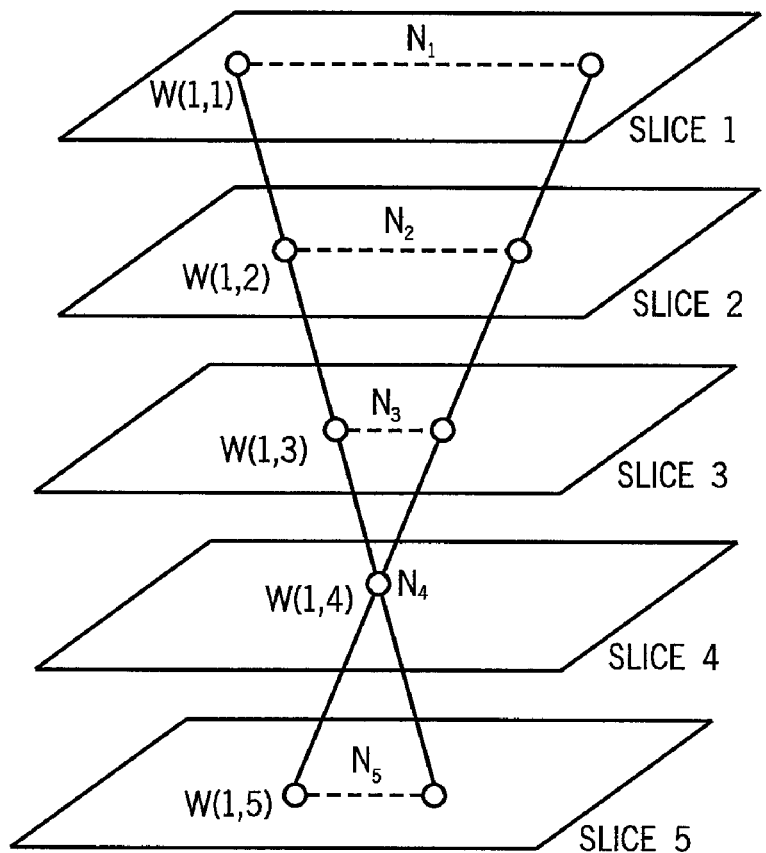
FIG. 3 illustrates a PSF based classification using intensity profiles across slices.
Figure 3B:
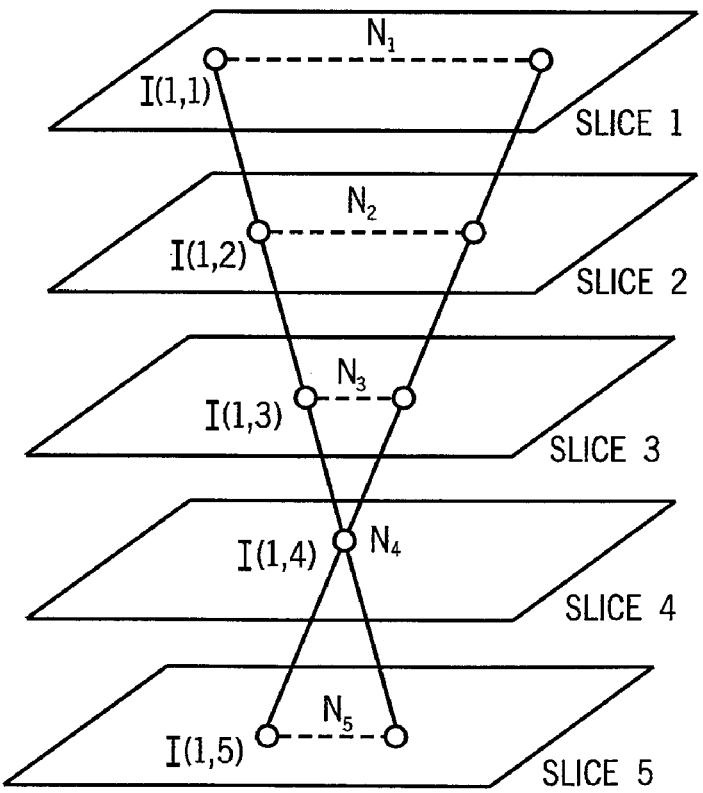
Figure 3C:
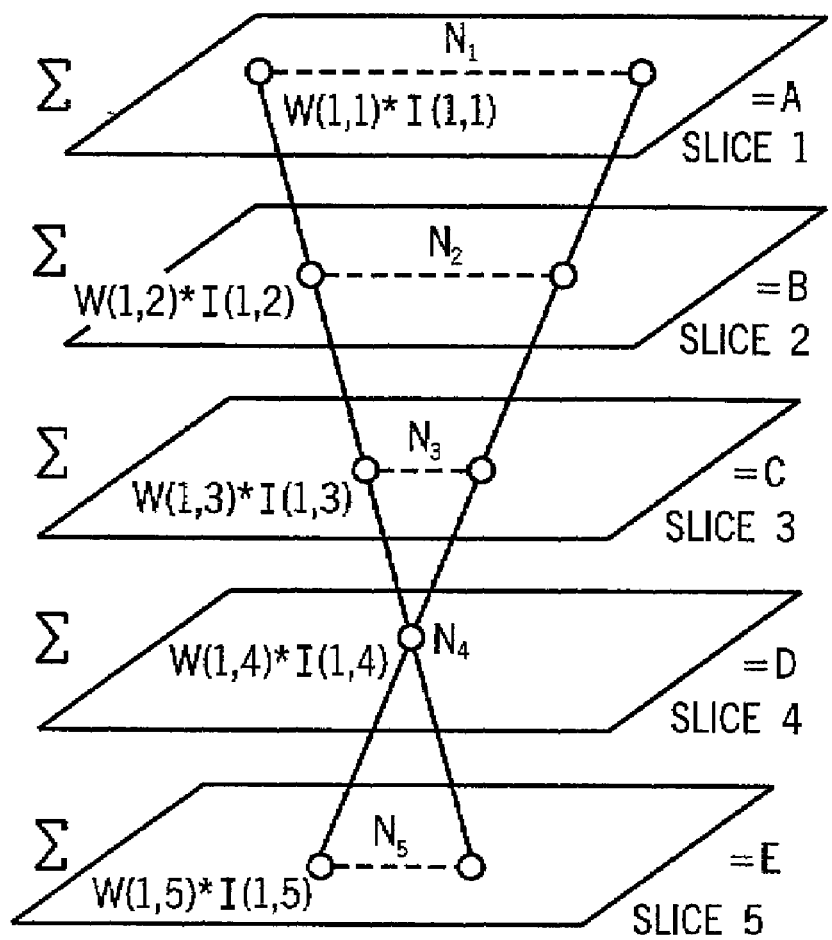

For every point in the volume, the integral of intensities contained within the line segment defined by the PSF was plotted at each slice. The method is pictorially represented in FIG. 3, along with the plot corresponding to the intensity profiles used for classification. Consider a tomosynthesis reconstructed dataset with five slices. For an arbitrary point in slice 4, the PSF is as shown in FIG. 3a. The corresponding intensity mask with the same shape and extent is shown in FIG. 3b. The result of a simple multiplication of these masks is represented in FIG. 3c. If N (slice) denotes the number of pixels in each slice within the PSF, W (pixel, slice) denotes the weight of a pixel in each slice and I (pixel, slice) denote the intensity of that pixel, then the mathematical formulation of this method can be given as:

$$\text{For slice 1:} \quad A = \sum_{x=1}^{N_1} (W_{(x,1)} * I_{(x,1)})$$

$$\text{For slice 2:} \quad B = \sum_{x=1}^{N_2} (W_{(x,2)} * I_{(x,2)})$$

$$\vdots \qquad \qquad \vdots$$

-continued $$\text{For slice 5:} \quad E = \sum_{x=1}^{N_5} (W_{(x,5)} * I_{(x,5)})$$

Figure 3D:
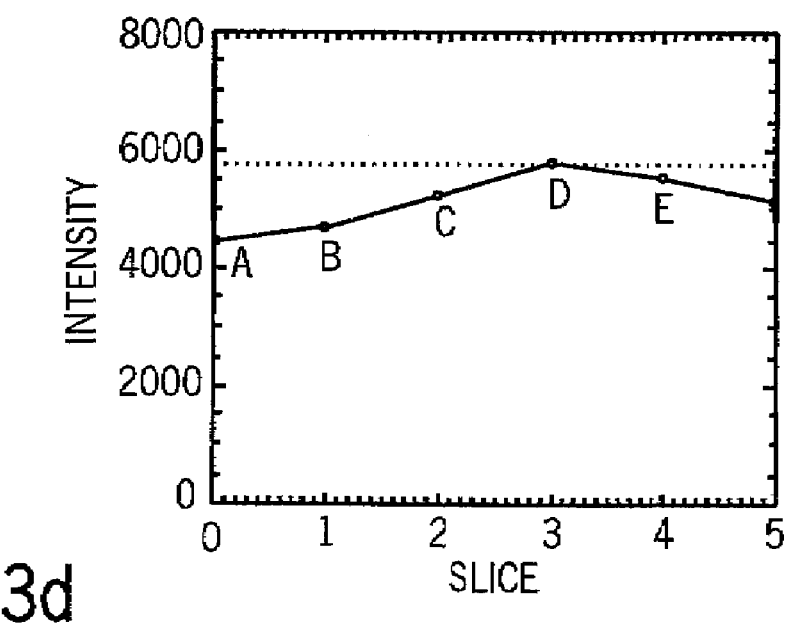
Figure 4A:
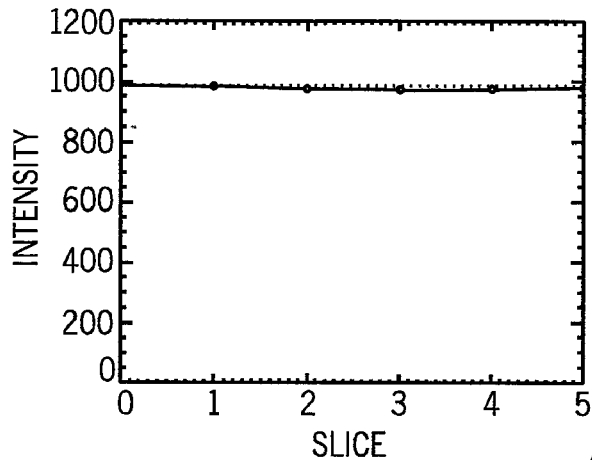
FIG. 4 illustrates intensity profiles representing (a) a background pixel, (b) an in-focus pixel, (c) an out-of-focus pixel, and (d) a low frequency pixel.
Figure 4B:
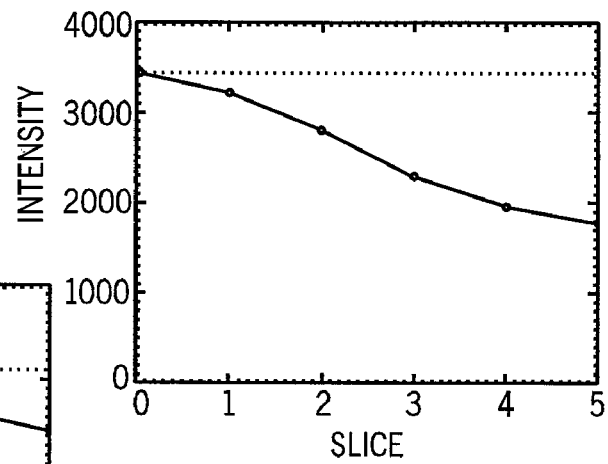
Figure 4C:
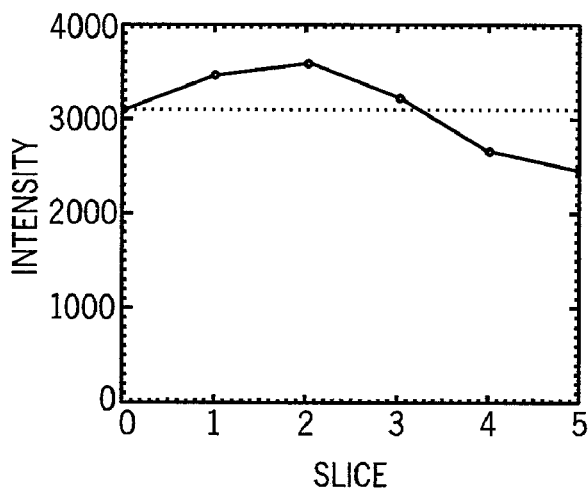
Figure 4D:
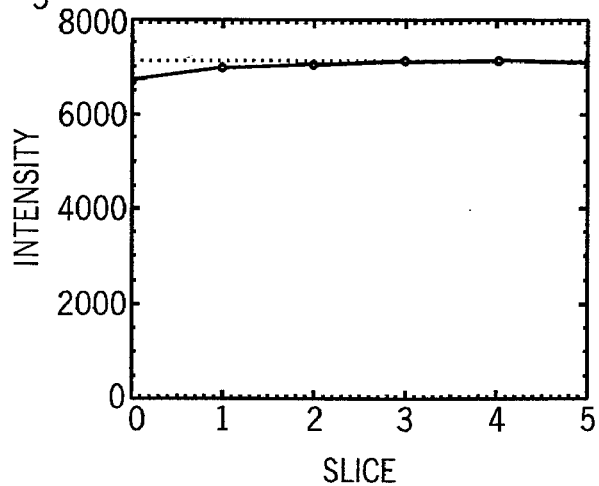

After summing the intensities for every slice, the resultants (A, B, C, D, E) are plotted as shown is FIG. 3d. The reference dotted line within the plot corresponds to the current intensity of that pixel. Every structure showed distinct but consistent characteristics for these profiles in the imaging volume. By analyzing the nature of intensity profiles for every pixel, one can classify them into in-focus, out-of-focus, background, and low-frequency details. Of course, other classification schemes exist. For example, one can classify the pixels (and regions of related pixels) as in-focus high-frequency, in-focus low-frequency, and so forth with different permutations.

At background and low-frequency pixels, the intensity plot showed flat curves with relatively low and high intensities respectively. At in-focus pixels, the maximum intensity of the plot coincided with the current intensity (slice 0) of that pixel and at out-of-focus pixels, the maximum intensity (slice 2) of the plot was greater than the current intensity (slice 0) of that pixel. After a first pass, the classification process was iteratively repeated over all pixels for a consistency check. A series of intensity plots for different categories is shown in FIG. 4.

Figure 5:
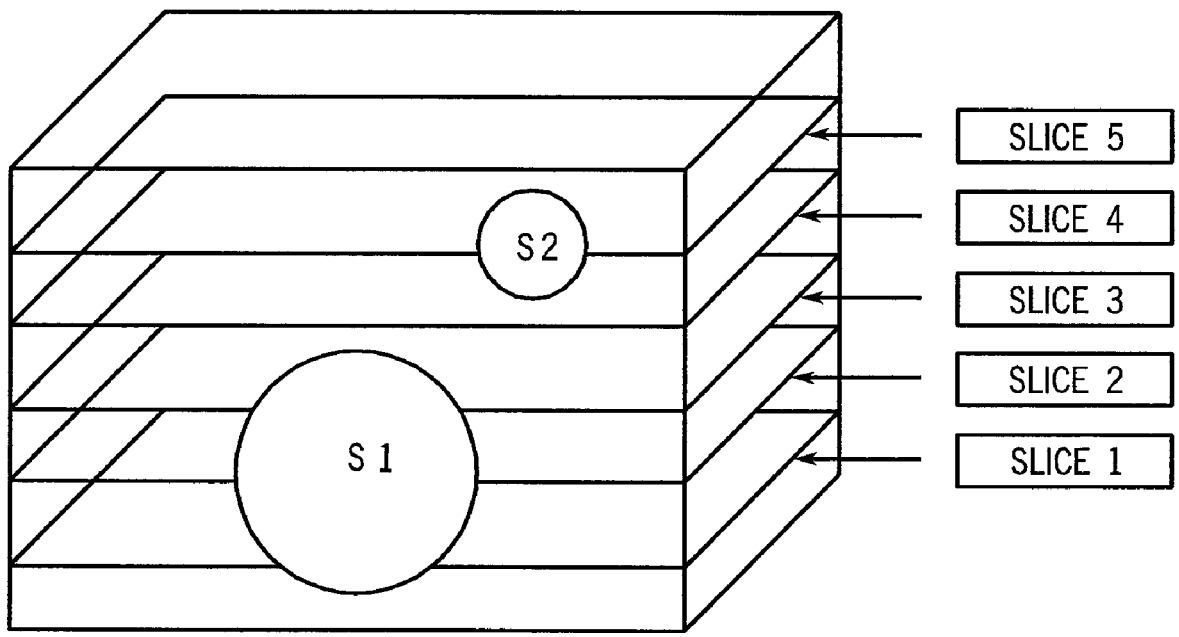
FIG. 5 illustrates a schematic model of the computer simulated sphere phantom.

The herein described methods and apparatus were validated using human observer classified regions as the "gold standard". A simulation phantom with two spheres was defined as shown in FIG. 5 and its regions were classified using intensity plots. Next, the computed classifications were compared with the gold standard, and based on that comparison, the sensitivity and specificity were defined for the method.

Figure 6A:
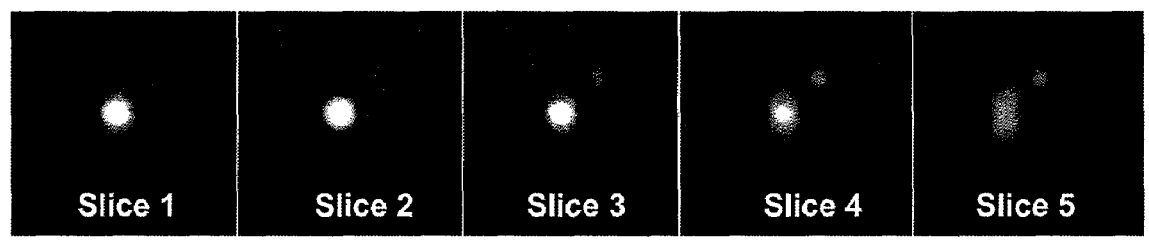
FIG. 6 illustrates (a) tomosynthesis slices reconstructed using a backprojection reconstruction algorithm and (b) PSF based classification of the simulation phantom.
Figure 6B:
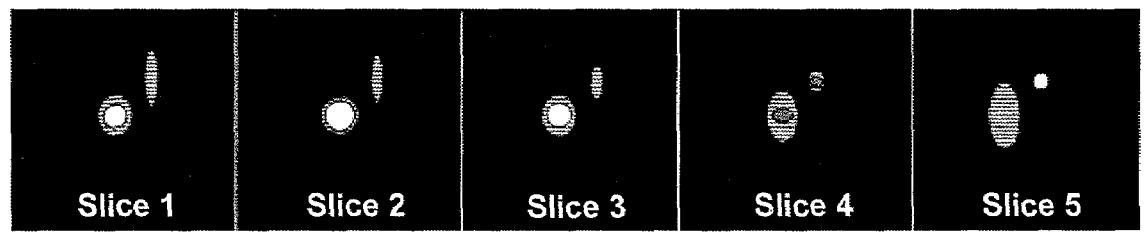

After classifying all pixels into respective categories for the computer simulated phantom, the reconstructed dataset was color coded for visual representation. Different gray-levels were used to mark the in-focus, out-of-focus, background, and low-frequency pixels. The results are shown in FIG. 6. The methods can be used an input for adaptive image processing as described in the accompanying disclosure co-filed with this disclosure as patent application Ser. No. 11/464,103.

One technical effect is that the herein described methods and apparatus provide the ability to classify structures (i.e., regions) based on the PSF and then one is able to selectively process the data differently for each different class if desired. This improved ability to differentiate between different classes of structures/regions leads to less artifacts and/or blurring in the final reconstructed images.

Exemplary embodiments are described above in detail. The assemblies and methods are not limited to the specific embodiments described herein, but rather, components of each assembly and/or method may be utilized independently and separately from other components described herein.

While the invention has been described in terms of various specific embodiments, those skilled in the art will recognize that the invention can be practiced with modification within the spirit and scope of the claims.

What is claimed is:
1. A computer readable medium embedded with a program configured to instruct a computer to use a point spread function based rule to classify regions of different intensity profiles in a tomosynthesis dataset.

2. A medium in accordance with claim 1 wherein said program further configured to instruct the computer to use the point spread function to classify structures in a tomosynthesis dataset.

3. A medium in accordance with claim 2 wherein the classification is into classes comprising a background class, an in-focus class, an out-of-focus class, and a low frequency class.

4. A medium in accordance with claim 1 wherein said program further configured to instruct the computer to generate a plurality of intensity profiles, one for each pixel.

5. A system comprising:
an x-ray source;
an x-ray detector positioned to receive x-rays emitted from said source; and
a computer operationally coupled to said source and said detector, said computer configured to use a point spread function based rule to classify regions of different intensity profiles in a tomosynthesis dataset.

6. A system in accordance with claim 5 wherein the classification is into classes comprising a background class, an in-focus class, an out-of-focus class, and a low frequency class.

7. A system in accordance with claim 5 wherein said computer further configured to generate a plurality of intensity profiles, one for each pixel.

8. A system in accordance with claim 5 wherein said computer further configured to provide visual indications on a reconstructed image of the different classifications.

9. A system in accordance with claim 8 wherein the classification is into classes comprising a background class, an in-focus class, an out-of-focus class, and a low frequency class.

10. A system in accordance with claim 9 wherein said computer further configured to generate a plurality of intensity profiles, one for each pixel.

11. A system in accordance with claim 10 wherein said computer further configured to use the point spread function to classify structures in a tomosynthesis dataset.

12. A method comprising:
providing an object to be scanned;
scanning the object to obtain a tomosynthesis dataset; and
using a point spread function based rule to classify regions of different intensity profiles in the tomosynthesis dataset.

13. A method in accordance with claim 12 wherein the dataset is a medical image dataset.

* * * * *